United States Patent
Rao et al.

(10) Patent No.: US 7,663,007 B2
(45) Date of Patent: Feb. 16, 2010

(54) PROCESS FOR THE PREPARATION OF 1,3,3,3-TETRAFLUOROPROPENE AND/OR 1,1,3,3,3-PENTAFLUOROPROPENE

(75) Inventors: Velliyur Nott Mallikarjuna Rao, Wilmington, DE (US); H. David Rosenfeld, Drumore, PA (US); Allen Capron Sievert, Elkton, MD (US); Shekhar Subramoney, Hockessin, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 43 days.

(21) Appl. No.: 11/988,259

(22) PCT Filed: Aug. 4, 2006

(86) PCT No.: PCT/US2006/030534

§ 371 (c)(1),
(2), (4) Date: Jan. 2, 2008

(87) PCT Pub. No.: WO2007/019358

PCT Pub. Date: Feb. 15, 2007

(65) Prior Publication Data

US 2009/0043138 A1    Feb. 12, 2009

Related U.S. Application Data

(60) Provisional application No. 60/706,160, filed on Aug. 5, 2005.

(51) Int. Cl.
*C07C 17/00* (2006.01)
(52) U.S. Cl. ........................................ 570/156; 570/175
(58) Field of Classification Search ................ 570/175, 570/156
See application file for complete search history.

(56) References Cited

U.S. PATENT DOCUMENTS

| 6,031,141 | A  | 2/2000  | Mallikarjuna et al. |
| 7,074,973 | B2 | 7/2006  | Nappa et al. |
| 7,129,383 | B2 | 10/2006 | Nappa et al. |
| 7,217,678 | B2 | 5/2007  | Rao et al. |
| 7,285,690 | B2 | 10/2007 | Rao et al. |
| 7,285,691 | B2 | 10/2007 | Rao et al. |
| 7,285,692 | B2 | 10/2007 | Rao et al. |
| 7,435,700 | B2 | 10/2008 | Amos et al. |
| 2003/0060670 | A1 | 3/2003  | Nair et al. |
| 2005/0227865 | A1 | 10/2005 | Nappa et al. |

FOREIGN PATENT DOCUMENTS

| WO | WO2005/037744 | 4/2005 |
| WO | WO2007/019353 | 2/2007 |
| WO | WO2007/019354 | 2/2007 |
| WO | WO2007/019355 | 2/2007 |
| WO | WO2007/019356 | 2/2007 |
| WO | WO2007/019357 | 2/2007 |
| WO | WO2007/019359 | 2/2007 |

OTHER PUBLICATIONS

U.S. Appl. No. 11/988,256, filed Feb. 15, 2007, Rao et al.
U.S. Appl. No. 11/988,436, filed Feb. 15, 2007, Rao et al.
U.S. Appl. No. 11/988,258, filed Feb. 15, 2007, Rao et al.
U.S. Appl. No. 11/988,200, filed Feb. 15, 2007, Rao et al.
U.S. Appl. No. 11/988,257, filed Feb. 15, 2007, Rao et al.
U.S. Appl. No. 11/988,983, filed Feb. 15, 2007, Rao et al.

*Primary Examiner*—Jafar Parsa

(57) ABSTRACT

A process for the manufacture of $CF_3CH=CHF$ and/or $CF_3CH=CF_2$ is disclosed. The process involves (a) reacting HF and at least one halopropene of the formula $CX_3CCl=CClX$ (where each X is independently F or Cl) to produce a product including both $CF_3CCl=CF_2$ and $CF_3CHClCF_3$; (b) reacting $CF_3CCl=CF_2$ and/or $CF_3CHClCF_3$ produced in (a) with hydrogen to produce a product including $CF_3CH_2CHF_2$ and/or $CF_3CH_2CF_3$; (c) dehydrofluorinating $CF_3CH_2CHF_2$ and/or $CF_3CH_2CF_3$ produced in (b) to produce a product comprising $CF_3CH=CHF$ and/or $CF_3CH=CF_2$; and (d) recovering $CF_3CH=CHF$ and/or $CF_3CH=CF_2$ from the product produced in (c). In (a), the $CF_3CCl=CF_2$ and $CF_3CHClCF_3$ are produced in the presence of a fluorination catalyst comprising at least one chromium-containing component selected from (i) a crystalline alpha-chromium oxide where at least 0.05 atom % of the chromium atoms in the alpha-chromium oxide lattice are replaced by divalent copper, and (ii) a chromium-containing composition of (i) which has been treated with a fluorinating agent.

4 Claims, No Drawings

PROCESS FOR THE PREPARATION OF 1,3,3,3-TETRAFLUOROPROPENE AND/OR 1,1,3,3,3-PENTAFLUOROPROPENE

This application represents a national filing under 35 U.S.C. 371 of International Application No. PCT/US2006/030534 filed Aug. 4, 2006, and claims priority of U.S. Provisional Application No. 60/706,160 filed Aug. 5, 2005.

FIELD OF THE INVENTION

This invention relates to the synthesis 1,3,3,3-tetrafluoropropene and 1,1,3,3,3-pentafluoropropene.

BACKGROUND

A number of chlorine-containing halocarbons are considered to be detrimental toward the Earth's ozone layer. There is a worldwide effort to develop materials having lower ozone depletion and global warming potential that can serve as effective replacements. For example, the hydrofluorocarbon, 1,1,1,2-tetrafluoroethane (HFC-134a) is being used as a replacement for dichlorodifluoromethane (CFC-12) in refrigeration systems. HFC-134a has a high global warming potential. There is a need for manufacturing processes that provide halogenated hydrocarbons that have lower ozone depletion and global warming potential. The production of hydrofluoroolefins (i.e., unsaturated compounds containing only carbon, hydrogen and fluorine), has been the subject of recent interest to provide environmentally desirable products for use as refrigerants, solvents, blowing agents, cleaning agents, aerosol propellants, heat transfer media, dielectrics, fire extinguishants, power cycle working fluids and polymer intermediates. For example, 1,3,3,3-tetrafluoropropene has utility as a refrigerant and 1,1,3,3,3-pentafluoropropene has utility as a monomer for the production of various polymers.

SUMMARY OF THE INVENTION

This invention provides a process for the manufacture of 1,3,3,3-tetrafluoropropene ($CF_3CH=CHF$ or HFC-1234ze) and/or 1,1,3,3,3-penta-fluoropropene ($CF_3CH=CF_2$ or HFC-1225zc). The process comprises (a) reacting HF and at least one halopropene of the formula $CX_3CCl=CClX$, wherein each X is independently selected from the group consisting of F and Cl, to produce a product comprising $CF_3CCl=CF_2$ and $CF_3CHClCF_3$, wherein said $CF_3CCl=CF_2$ and $CF_3CHClCF_3$ are produced in the presence of a fluorination catalyst comprising at least one chromium-containing component selected from (i) a crystalline alpha-chromium oxide where at least 0.05 atom % of the chromium atoms in the alpha-chromium oxide lattice are replaced by divalent copper, and (ii) a chromium-containing composition of (i) which has been treated with a fluorinating agent (e.g., anhydrous hydrogen fluoride); (b) reacting $CF_3CCl=CF_2$ and/or $CF_3CHClCF_3$ produced in (a) with hydrogen ($H_2$), optionally in the presence of HF, to produce a product comprising $CF_3CH_2CHF_2$ and/or $CF_3CH_2CF_3$; (c) dehydrofluorinating $CF_3CH_2CHF_2$ and/or $CF_3CH_2CF_3$ produced in (b), to produce a product comprising $CF_3CH=CHF$ and/or $CF_3CH=CF_2$; and (d) recovering $CF_3CH=CHF$ and/or $CF_3CH=CF_2$ from the product produced in (c).

DETAILED DESCRIPTION

This invention provides a process for the preparation of $CF_3CH=CHF$ (that can be present as the E- and Z-forms of isomers) and/or $CF_3CH=CF_2$. The HFC-1234ze and HFC-1225zc may be recovered as individual products and/or as one or more mixtures of the two products.

In step (a) of the process of this invention, one or more halopropene compounds $CX_3CCl=CClX$, wherein each X is independently selected from the group consisting of F and Cl, are reacted with hydrogen fluoride (HF) to produce a product mixture comprising $CF_3CCl=CF_2$ (CFC-1215xc) and $CF_3CHClCF_3$ (HCFC-226da). Step (a) may be operated to produce primarily either one of these two compounds, or to produce a mixture containing significant quantities of both of these compounds. Accordingly, this invention provides a process for the preparation of mixtures of $CF_3CCl=CF_2$ (CFC-1215xc) and $CF_3CHClCF_3$ (HCFC-226da) from readily available starting materials.

Suitable starting materials for the process of this invention include E- and Z-$CF_3CCl=CClF$ (CFC-1214xb), $CF_3CCl=CCl_2$ (CFC-1213xa), $CClF_2CCl=CCl_2$ (CFC-1212xa), $CCl_2FCCl=CCl_2$ (CFC-1211xa), and $CCl_3CCl=CCl_2$ (hexachloropropene, HCP), or mixtures thereof.

Due to their availability, $CF_3CCl=CCl_2$ (CFC-1213xa) and $CCl_3CCl=CCl_2$ (hexachloropropene, HCP) are preferred starting materials for the process of the invention.

Preferably, the reaction of HF with $CX_3CCl=CClX$ is carried out in the vapor phase in a heated tubular reactor. A number of reactor configurations are possible, including vertical and horizontal orientation of the reactor and different modes of contacting the halopropene starting material(s) with HF. Preferably the HF is substantially anhydrous.

In one embodiment of step (a), the halopropene starting material(s) may be fed to the reactor containing the fluorination catalyst. The halopropene starting material(s) may be initially vaporized and fed to the reactor as gas(es).

In another embodiment of step (a), the halopropene starting material(s) may be contacted with HF in a pre-reactor. The pre-reactor may be empty (i.e., unpacked), but is preferably filled with a suitable packing such as Monel™ or Hastelloy™ nickel alloy turnings or wool, or other material inert to HCl and HF which allows efficient mixing of $CX_3CCl=CClX$ and HF.

If the halopropene starting material(s) are fed to the pre-reactor as liquid(s), it is preferable for the pre-reactor to be oriented vertically with $CX_3CCl=CClX$ entering the top of the reactor and pre-heated HF vapor introduced at the bottom of the reactor.

Suitable temperatures for the pre-reactor are within the range of from about 80° C. to about 250° C., preferably from about 100° C. to about 200° C. Under these conditions, for example, hexachloropropene is converted to a mixture containing predominantly CFC-1213xa. The starting material feed rate is determined by the length and diameter of the reactor, the temperature, and the degree of fluorination desired within the pre-reactor. Slower feed rates at a given temperature will increase contact time and tend to increase the amount of conversion of the starting material and increase the degree of fluorination of the products.

The term "degree of fluorination" means the extent to which fluorine atoms replace chlorine substituents in the $CX_3CCl=CClX$ starting materials. For example, $CF_3CCl=CClF$ represents a higher degree of fluorination than $CClF_2CCl=CCl_2$ and $CF_3CHClCF_3$ represents a higher degree of fluorination than $CClF_2CHClCF_3$.

The molar ratio of HF fed to the pre-reactor, or otherwise to the reaction zone of step (a), to halopropene starting material fed in step (a), is typically from about stoichiometric to about 50:1. The stoichiometric ratio depends on the average degree of fluorination of the halopropene starting material(s) fed to the pre-reactor and is typically based on formation of $C_3ClF_5$. For example, if the halopropene is HCP, the stoichiometric ratio of HF to HCP is 5:1; if the halopropene is CFC-1213xa, the stoichiometric ratio of HF to CFC-1213xa is 2:1. Preferably, the molar ratio of HF to halopropene starting material is from about twice the stoichiometric ratio (based on formation of $C_3ClF_5$) to about 30:1. Higher ratios than 30:1 are not particularly beneficial. Lower ratios of HF to halopropene result in reduced yields of CFC-1215xc and HCFC-226da. Typically, for a given catalyst, higher HF feed ratios will tend to favor formation of HCFC-226da relative to CFC-1215xc.

In a preferred embodiment of this invention, in step (a) of the process, the halopropene starting materials are vaporized, preferably in the presence of HF, contacted with HF in a pre-reactor, and then contacted with the fluorination catalyst. If the preferred amount of HF is fed in the pre-reactor, additional HF is not required when the effluent from the pre-reactor contacts the fluorination catalyst.

Suitable temperatures for catalytic fluorination of halopropene starting materials and/or their products formed in the pre-reactor are within the range of about 200° C. to about 400° C., preferably from about 240° C. to about 350° C. Higher temperatures typically contribute to reduced catalyst life. Temperatures below about 240° C. may result in substantial amounts of products having a degree of fluorination less than five (i.e., underfluorinates). Suitable reactor pressures for vapor phase embodiments of this invention may be in the range of from about 1 to about 30 atmospheres. Reactor pressures of about 5 atmospheres to about 20 atmospheres may be advantageously employed to facilitate separation of HCl from other reaction products.

The fluorination catalysts which are used in the process of the present invention are preferably compositions comprising crystalline $\alpha$-$Cr_2O_3$ ($\alpha$-chromium oxide) in which some of the chromium(III) ions have been substituted by copper(II) ions or compositions obtained by treatment of said compositions with a fluorinating agent. Of note are embodiments containing at least 1 atom % copper based on the total of the copper and chromium in the alpha-chromium oxide. The amount of copper relative to the total of chromium and copper in the alpha-chromium oxide of these compositions is preferably from about 1 atom % to about 5 atom %. Of particular note are embodiments containing from about 2 atom % to about 3 atom % copper based on the total of the copper and chromium in the alpha-chromium oxide.

These compositions may be prepared, for example, by co-precipitation methods followed by calcination.

In a typical co-precipitation procedure, an aqueous solution of copper and chromium(III) salts is prepared. The relative concentrations of the copper and chromium(III) salts in the aqueous solution is dictated by the bulk atom percent copper relative to chromium desired in the final catalyst. Therefore, the concentration of copper in the aqueous solution is preferably from 1 atom % to about 5 atom % of the total concentration of copper and chromium in the solution. The concentration of chromium(III) in the aqueous solution is typically in the range of 0.3 to 3 moles per liter with 0.75-1.5 moles per liter being a preferred concentration. While different chromium(III) salts might be employed, chromium(III) nitrate or its hydrated forms such as $[Cr(NO_3)_3(H_2O)_9]$, are the most preferred chromium(III) salts for preparation of said aqueous solution.

While different copper salts might be employed for preparation of said aqueous solutions, preferred copper salts for preparation of catalysts for the process of this invention include copper(II) nitrate and its hydrated forms such as $[Cu(NO_3)_2(H_2O)_{2.5}]$ and copper(II) chloride.

The aqueous solution of the chromium(III) and copper salts may then be evaporated either under vacuum or at elevated temperature to give a solid which is then calcined.

It is preferred to treat the aqueous solution of the chromium (III) and copper salts with a base such as ammonium hydroxide (aqueous ammonia) to precipitate the copper and chromium as the hydroxides. Bases containing alkali metals such as sodium or potassium hydroxide or the carbonates may be used but are not preferred. The addition of ammonium hydroxide to the aqueous solution of the chromium(III) and copper salts is typically carried out gradually over a period of 1 to 12 hours. The pH of the solution is monitored during the addition of base. The final pH is typically in the range of 6.0 to 11.0, preferably from about 7.5 to about 9.0, most preferably about 8.0 to about 8.7. The precipitation of the copper and chromium hydroxide mixture is typically carried out at a temperature of about 15° C. to about 60° C., preferably from about 20° C. to about 40° C. After the ammonium hydroxide is added, the mixture is typically stirred for up to 24 hours. The precipitated chromium and copper hydroxides serve as precursors to the catalysts of the invention.

After the precipitation of the copper and chromium hydroxide mixture is complete, the mixture is dried. This may be carried out by evaporation in an open pan on a hot plate or steam bath or in an oven or furnace at a suitable temperature. Suitable temperatures include temperatures from about 60° C. to about 130° C. (for example, about 100° C. to about 120° C.). Alternatively, the drying step may be carried out under vacuum using, for example, a rotary evaporator.

Optionally, the precipitated copper and chromium hydroxide mixture may be collected and, if desired, washed with deionized water before drying. Preferably the precipitated copper and chromium hydroxide mixture is not washed prior to the drying step.

After the copper and chromium hydroxide mixture has been dried, the nitrate salts are then decomposed by heating the solid from about 250° C. to about 350° C. The resulting solid is then calcined at temperatures of from about 400° C. to about 1000° C., preferably from about 400° C. to about 900° C.

The copper-substituted alpha-chromium oxide compositions may also be prepared by a thermal method. In this method, a solution of the copper and chromium(III) salt is prepared as described for the co-precipitation technique. The mixed solution of the salts is then evaporated under atmospheric pressure or reduced pressure to give a solid. The solid is then placed in a furnace and the temperature raised gradually to decompose the salt. It is preferred to use the nitrate salts that decompose to the oxide. After decomposition of the nitrate salts is complete (about 350° C.), the increase in temperature is continued till the desired calcination temperature is reached. The desired calcination temperature is between about 450° C. to about 1000° C., a temperature of about 450° C. to about 900° C. being preferred. After the desired calcination temperature is reached, the solid is maintained at this temperature for an additional 8 to 24 hours, about 8 to about 12 hours being preferred. The decomposition and calcination is preferably carried out in the presence of oxygen, most preferably in the presence of air.

Further information on the copper and chromium compositions useful for this invention is provided in U. S. patent application Ser. No. 60/706,159 filed Aug. 5, 2005, and hereby incorporated by reference herein in its entirety.

The calcined copper-substituted alpha-chromium oxide compositions used in the present invention may be pressed into various shapes such as pellets for use in packing reactors. It may also be used in powder form.

Typically, the calcined compositions will be pre-treated with a fluorinating agent prior to use as catalysts for changing the fluorine content of halogenated carbon compounds. Typically this fluorinating agent is HF though other materials may be used such as sulfur tetrafluoride, carbonyl fluoride, and fluorinated carbon compounds such as trichlorofluoromethane, dichlorodifluoromethane, chlorodifluoromethane, trifluoromethane, or 1,1,2-trichlorotrifluoroethane. This pretreatment can be accomplished, for example, by placing the catalyst in a suitable container which can be the reactor to be used to perform the process of the instant invention, and thereafter, passing HF over the dried, calcined catalyst so as to partially saturate the catalyst with HF. This is conveniently carried out by passing HF over the catalyst for a period of time, for example, about 0.1 to about 10 hours at a temperature of, for example, about 200° C. to about 450° C. Nevertheless, this pretreatment is not essential.

Compounds that are produced in the fluorination process in step (a) include the $CF_3CCl=CF_2$ (CFC-1215xc) and $CF_3CHClCF_3$ (HCFC-226da).

Halopropane by-products having a higher degree of fluorination than HCFC-226da that may be formed in step (a) include $CF_3CClFCF_3$ (CFC-217ba).

Halopropane by-products having a lower degree of fluorination than HCFC-226da that may be formed in step (a) include $CF_3CHClCClF_2$ (HCFC-225da) and $CF_3CHClCCl_2F$ (HCFC-224db). Other halopropane by-products which may be formed include CFC-216aa ($CF_3CCl_2CF_3$).

Halopropene by-products having a lower degree of fluorination than CFC-1215xc that may be formed in step (a) include E- and Z—$CF_3CCl=CClF$ (CFC-1214xb) and $CF_3CCl=CCl_2$ (CFC-1213xa).

Typically, the effluent from step (a) comprising CFC-1215xc and HCFC-226da, and optionally HF, is separated from lower boiling components, mainly comprising HCl along with some over-fluorinated products such as CFC-217ba and azeotropic HF, and from the higher boiling components comprising the under-fluorinated components such as HCFC-225da, $C_3Cl_4F_4$ isomers, and CFC-1213xa.

In one embodiment of the process of this invention, the reactor effluent from step (a) may be delivered to a distillation column in which HCl and any HCl azeotropes are removed from the top of column while the higher boiling components are removed at the bottom of the column. The products recovered at the bottom of the first distillation column are then delivered to a second distillation column in which CFC-217ba, and some HF, are separated at the top of the column and the remaining HF and organic products, comprising $CF_3CHClCF_3$, $CF_3CCl=CF_2$, and higher boiling components, are removed from the bottom of the column. The products recovered from the bottom of the second distillation column are then delivered to a third distillation column in which $CF_3CHClCF_3$, $CF_3CCl=CF_2$, and HF, are separated at the top of the column, and any remaining HF and under-fluorinated components are removed from the bottom of the column.

The mixture of $CF_3CHClCF_3$, $CF_3CCl=CF_2$, and HF, from the top of the third distillation column may be delivered to step (b) or may optionally be delivered to a decanter maintained at a suitable temperature to cause separation of an organic-rich liquid phase and an HF-rich liquid phase. The HF-rich phase may be distilled to recover HF that is then recycled to step (a). The organic-rich phase may then be delivered to step (b) or may be distilled to give pure HCFC-226da and CFC-1215xc.

In one embodiment of the process of this invention, said under-fluorinated components such as HCFC-225da, $C_3Cl_2F_4$, and $CF_3CCl=CCl_2$ (CFC-1213xa) may be returned to step (a).

In step (b) of the process, the $CF_3CHClCF_3$ and/or $CF_3CCl=CF_2$ produced in step (a) are reacted with hydrogen ($H_2$), optionally in the presence of HF.

In a preferred embodiment of the process, the reacting of hydrogen with the CFC-1215xc/HCFC-226da mixture produced in step (a), and optionally HF, is carried out in the presence of a hydrogenation catalyst. Hydrogenation catalysts suitable for use in this embodiment include catalysts comprising at least one metal selected from the group consisting of rhenium, iron, ruthenium, osmium, cobalt, rhodium, iridium, nickel, palladium, and platinum. Said catalytic metal component is typically supported on a carrier such as carbon or graphite or a metal oxide, fluorinated metal oxide, or metal fluoride where the carrier metal is selected from the group consisting of magnesium, aluminum, titanium, vanadium, chromium, iron, and lanthanum. Of note are catalysts of palladium supported on carbon (see e.g., U.S. Pat. No. 5,523,501, the teachings of which are incorporated herein by reference).

Of note are carbon-supported catalysts in which the carbon support has been washed with acid and has an ash content below about 0.1% by weight. Hydrogenation catalysts supported on low ash carbon are described in U.S. Pat. No. 5,136,113, the teachings of which are incorporated herein by reference. Also of note are catalysts comprising at least one metal selected from the group consisting of palladium, platinum, and rhodium supported on alumina ($Al_2O_3$), fluorinated alumina, or aluminum fluoride ($AlF_3$).

The supported metal catalysts may be prepared by conventional methods known in the art such as by impregnation of the carrier with a soluble salt of the catalytic metal (e.g., palladium chloride or rhodium nitrate) as described by Satterfield on page 95 of *Heterogenous Catalysis in Industrial Practice*, $2^{nd}$ edition (McGraw-Hill, New York, 1991). The concentration of the catalytic metal(s) on the support is typically in the range of about 0.1% by weight of the catalyst to about 5% by weight.

The relative amount of hydrogen contacted with CFC-1215xc and HCFC-226da when a hydrogenation catalyst is used is typically from about the stoichiometric ratio of hydrogen to $CF_3CHClCF_3/CF_3CCl=CF_2$ mixture to about 10 moles of $H_2$ per mole of $CF_3CHClCF_3/CF_3CCl=CF_2$ mixture. The stoichiometric ratio of hydrogen to the $CF_3CHClCF_3/CF_3CCl=CF_2$ mixture depends on the relative amounts of the two components in the mixture. The stoichiometric amounts of $H_2$ required to convert HCFC-226da and CFC-1215xc to $CF_3CH_2CF_3$ and $CF_3CH_2CHF_2$, are one and two moles, respectively.

Suitable temperatures for the catalytic hydrogenation are typically from about 100° C. to about 350° C., preferably from about 125° C. to about 300° C. Temperatures above about 350° C. tend to result in defluorination side reactions; temperatures below about 125° C. will result in incomplete substitution of Cl for H in the starting materials. The reactions are typically conducted at atmospheric pressure or superatmospheric pressure.

The products from the step (b) reaction zone(s) typically include HCl, $CF_3CH_2CF_3$ (HFC-236fa), $CF_3CH_2CHF_2$ (HFC-245fa), and small amounts of lower boiling by-products (typically including propane, $CF_3CH=CF_2$ (HFC- 1225zc), E- and Z-$CF_3CH=CHF$ (HFC-1234ze), and/or $CF_3CH_2CH_3$ (HFC-263fb) and higher boiling by-products and intermediates (typically including $CF_3CHFCH_3$ (HFC-254eb) and/or $CF_3CHClCHF_2$ (HCFC-235da) as well as any unconverted starting materials and any HF carried over from step (a).

In step (c) of the process, $CF_3CH_2CHF_2$ and/or $CF_3CH_2CF_3$ produced in step (b) are dehydrofluorinated.

In one embodiment of step (c), a mixture comprising $CF_3CH_2CHF_2$ and $CF_3CH_2CF_3$, and optionally an inert gas, is delivered in the vapor phase to a dehydrofluorination catalyst as described in U. S. Pat. No. 6,369,284; the teachings of this disclosure are incorporated herein by reference. Dehydrofluorination catalysts suitable for use in this embodiment include (1) at least one compound selected from the oxides, fluorides and oxyfluorides of magnesium, zinc and mixtures of magnesium and zinc, (2) lanthanum oxide, (3) fluorided lanthanum oxide, (4) activated carbon, and (5) three-dimensional matrix carbonaceous materials.

The catalytic dehydrofluorination of $CF_3CH_2CHF_2$ and $CF_3CH_2CF_3$ is suitably conducted at a temperature in the range of from about 200° C. to about 500° C., and preferably from about 350° C. to about 450° C. The contact time is typically from about 1 to about 450 seconds, preferably from about 10 to about 120 seconds.

The reaction pressure can be subatmospheric, atmospheric or superatmospheric. Generally, near atmospheric pressures are preferred. However, the dehydrofluorination of $CF_3CH_2CHF_2$ and $CF_3CH_2CF_3$ can be beneficially run under reduced pressure (i.e., pressures less than one atmosphere).

The catalytic dehydrofluorination can optionally be carried out in the presence of an inert gas such as nitrogen, helium or argon. The addition of an inert gas can be used to increase the extent of dehydrofluorination. Of note are processes where the mole ratio of inert gas to $CF_3CH_2CHF_2$ and/or $CF_3CH_2CF_3$ is from about 5:1 to 1:1. Nitrogen is the preferred inert gas.

The products from the step (c) reaction zone typically include HF, E- and Z-forms of $CF_3CH=CHF$ (HFC-1234ze), $CF_3CH=CF_2$ (HFC-1225zc), $CF_3CH_2CHF_2$, $CF_3CH_2CF_3$ and small amounts of other products. Unconverted $CF_3CH_2CHF_2$ and $CF_3CH_2CF_3$ may be recycled back to the dehydrofluorination reactor to produce additional quantities of $CF_3CH=CHF$ and $CF_3CH=CF_2$.

In another embodiment of step (c), the $CF_3CH_2CHF_2$ and $CF_3CH_2CF_3$ are subjected to dehydrofluorination at an elevated temperature in the absence of a catalyst as disclosed in U.S. patent application Ser. No.60/623,210 filed Oct. 29, 2004, the teachings of which are incorporated herein by reference. The reactor can be fabricated from nickel, iron, titanium, or their alloys, as described in U. S. Pat. No. 6,540,933; the teachings of this disclosure are incorporated herein by reference. A reaction vessel of these materials (e.g., a metal tube) optionally packed with the metal in suitable form may also be used. When reference is made to alloys, it is meant a nickel alloy containing form 1 to 99.9% (by weight) nickel, an iron alloy containing 0.2 to 99.8% (by weight) iron, and a titanium alloy containing 72-99.8% (by weight) titanium. Of note is use of an empty (unpacked) reaction vessel made of nickel or alloys of nickel such as those containing 40% to 80% nickel, e.g., Inconel™ 600 nickel alloy, Hastelloy™ C617 nickel alloy, or Hastelloy™ C276 nickel alloy.

When used for packing, the metal or metal alloys may be particles or formed shapes such as perforated plates, rings, wire, screen, chips, pipe, shot, gauze, or wool.

The temperature of the reaction in this embodiment can be between about 350° C. and about 900° C., and is preferably at least about 450° C.

In yet another embodiment of step (c), the $CF_3CH_2CHF_2$ and $CF_3CH_2CF_3$ are first separated as individual compounds and subjected to dehydrofluorination in the presence or absence of a catalyst.

Step (d) of the process involves recovery of the desired product(s). Products from step (c) may be delivered to a separation unit to recover $CF_3CH=CHF$ and $CF_3CH=CF_2$ individually or as mixtures of $CF_3CH=CHF$ and $CF_3CH=CF_2$ by known procedures such as distillation. In one embodiment both $CF_3CH=CHF$ and $CF_3CH=CF_2$ are recovered. In another embodiment where both $CF_3CH=CHF$ and $CF_3CH=CF_2$ are produced in step (c), $CF_3CH=CF_2$ is recovered and $CF_3CH=CHF$ is further processed to produce $CF_3CH_2CH_2F$ (HFC-254fb) by hydrogenation. The $CF_3CH_2CH_2F$ can then be dehydrofluorinated to produce $CF_3CH=CH_2$. In yet another embodiment where both $CF_3CH=CHF$ and $CF_3CH=CF_2$ are produced in step (c), $CF_3CH=CHF$ is recovered and $CF_3CH=CF_2$ is returned to the step (b) reaction zone to produce additional $CF_3CH_2CHF_2$ (HFC-245fa) by hydrogenation. Hydrogenation and dehydrofluorination are known processes, and may be implemented in a manner analogous to the hydrogenation and dehydrofluorination steps described above.

The reactor, distillation columns, and their associated feed lines, effluent lines, and associated units used in applying the processes of this invention should be constructed of materials resistant to hydrogen fluoride and hydrogen chloride. Typical materials of construction, well-known to the fluorination art, include stainless steels, in particular of the austenitic type, the well-known high nickel alloys, such as Monel™ nickel-copper alloys, Hastelloy™ nickel-based alloys and, Inconel™ nickel-chromium alloys, and copper-clad steel.

The following specific embodiments are to be construed as merely illustrative, and do not constrain the remainder of the disclosure in any way whatsoever.

EXAMPLES

Catalyst Preparations

Comparative Preparation Example 1

Preparation of 100% Chromium Catalyst

A solution of 400 g $Cr(NO_3)_3[9(H_2O)]$ (1.0 mole) in 1000 mL of deionized water was treated dropwise with 477 mL of 7.4M aqueous ammonia raising the pH to about 8.5. The slurry was stirred at room temperature overnight. After re-adjusting the pH to 8.5 with ammonia, the mixture was poured into evaporating dishes and dried in air at 120° C. The dried solid was then calcined in air at 400° C.; the resulting solid weighed 61.15 g. The catalyst was pelletized (−12 to +20 mesh, 1.68 to 0.84 mm)) and 28.2 g (20 mL) was used in Comparative Example 1.

Preparation Example 1

Preparation of 99% Chromium/1% Copper Catalyst

To a one liter beaker containing 261.0 g $Cr(NO_3)_3[9(H_2O)]$ (0.652 mole) and 1.46 g $Cu(NO_3)_2[2.5\ H_2O]$ (0.0063 mole) was added 100 mL of deionized water. The slurry was placed on a stirring hot plate in a fume-hood and heated while stirring until oxides of nitrogen started to evolve. The beaker containing the paste-like material was placed in a furnace in the fume-hood after removing the stirrer. The temperature of the furnace was raised to 150° C. at the rate of 10 degrees/min and then to 550° C. at the rate of 1 degree/minute. It was held at 550° C. for an additional 10 hours. The resulting solid was pelletized (−12 to +20 mesh, 1.68 to 0.84 mm)) and 12.6 g (8.0 mL) was used in Example 1.

Preparation Example 2

Preparation of 99% Chromium/1% Copper Catalyst

In a 2000 mL beaker was placed 400.2 g $Cr(NO_3)_3[9(H_2O)]$ (1.0 mole) and 1.64 g $CuCl_2$ (0.012 mole). To the solids was added 1000 mL deionized water. The mixture was stirred and when the dissolution was complete, the pH of the solution was raised from 2.0 to 8.0 by drop-wise addition of 8 molar aqueous ammonium hydroxide. The precipitated slurry was stirred for 24 hours at room temperature. It was then dried at 120-130° C. overnight and calcined at 450° C. for an additional 24 hours in air. The resulting solid was pelletized (−12 to +20 mesh, 1.68 to 0.84 mm)) and 11.0 g (8.0 mL) was used in Example 2.

Preparation Example 3

Preparation of 99% Chromium/1% Copper Catalyst

In a 3000 mL beaker was placed 500.0 g $Cr(NO_3)_3[9(H_2O)]$ (1.25 moles) and 3.05 g $Cu(NO_3)_2[2.5\ H_2O$ (0.013 mole). To the solids was added 1200 mL deionized water. The mixture was stirred and when the dissolution was complete, the pH of the solution was raised from 2.4 to 8.5 by drop-wise addition of 300 mL of 8 molar aqueous ammonium hydroxide. The precipitated slurry was stirred for 24 hours at room temperature. It was then dried at 110-120° C. overnight and calcined at 500° C. for an additional 24 hours in air. The resulting solid was pelletized (−12 to +20 mesh, 1.68 to 0.84 mm)) and 16.0 g (8.0 mL) was used in Example 3.

Preparation Example 4

Preparation of 98% Chromium/2% Copper Catalyst

Preparation Example 1 was substantially repeated except that the amount of chromium(III) nitrate was 258.0 g (0.645 mole) and the amount of copper(II) nitrate was 2.9 g (0.0125 mole). The resulting solid was pelletized (−12 to +20 mesh, 1.68 to 0.84 mm)) and 12.6 g (8.0 mL) was used in Example 4.

Preparation Example 5

Preparation of 98% Chromium/2% Copper Catalyst

Preparation Example 2 was substantially repeated with 400.2 g chromium(III) nitrate (1.0 mole) and 3.31 g (0.0246 mole) copper(II) chloride. The solid, calcined in air at 450° C. for 24 hours, was pelletized (−12 to +20 mesh, 1.68 to 0.84 mm)) and 10.9 g (8.0 mL) was used in Example 5.

Preparation Example 6

Preparation of 98% Chromium/2% Copper Catalyst

In a 3000 mL beaker was placed 500.0 g $Cr(NO_3)_3[9(H_2O)]$ (1.1.25 mole) and 6.1 g $Cu(NO_3)_2[2.5\ H2O$ (0.0262 mole). To the solids was added 1200 mL deionized water. The mixture was stirred and when the dissolution was complete, the pH of the solution was raised from 2.4 to 8.2 by drop-wise addition of 300 mL 8 molar aqueous ammonium hydroxide. The precipitated slurry was stirred for 24 hours at room temperature. It was then dried at 110-120° C. overnight and calcined at 500° C. for an additional 24 hours in air. The resulting solid was pelletized (−12 to +20 mesh, 1.68 to 0.84 mm)) and 14.9 g (8.0 mL) was used in Example 6 as the catalyst.

Examples 1-6 and Comparative Example 1

General Procedure for Fluorination

A weighed quantity of pelletized catalyst was placed in a 5/8 inch (1.58 cm) diameter Inconel™ nickel alloy reactor tube heated in a fluidized sand bath. The tube was heated from 50° C. to 175° C. in a flow of nitrogen (50 cc/min; $8.3(10)^{-7}m^3$/sec) over the course of about one hour. HF was then admitted to the reactor at a flow rate of 50 cc/min ($8.3(10)^{-7}m^3$/sec). After 0.5 to 2 hours the nitrogen flow was decreased to 20 cc/min ($3.3(10)^{-7}m^3$/sec) and the HF flow increased to 80 cc/min ($1.3(10)^{-6}m^3$/sec); this flow was maintained for about 1 hour. The reactor temperature was then gradually increased to 400° C. over 3 to 5 hours. At the end of this period, the HF flow was stopped and the reactor cooled to 300° C. under 20 sccm ($3.3(10)^{-7}m^3$/sec) nitrogen flow. CFC-1213xa was fed from a pump to a vaporizer maintained at about 118° C. The CFC-1213xa vapor was combined with the appropriate molar ratios of HF in a 0.5 inch (1.27 cm) diameter Monel™ nickel alloy tube packed with Monel™ turnings. The mixture of reactants then entered the reactor. The HF/1213xa molar ratio was 20 and the contact time was 5 seconds for all Examples unless otherwise indicated. All reactions were conducted at a nominal pressure of one atmosphere. The results of CFC-1213xa fluorination over several catalysts are shown in Table 1. Analytical data for identified compounds is given in units of GC area %. Small quantities of other unidentified products were present.

General Procedure for Product Analysis

The following general procedure is illustrative of the method used for analyzing the products of fluorination reactions. Part of the total reactor effluent was sampled on-line for organic product analysis using a gas chromatograph equipped a mass selective detector (GC-MS). The gas chromatography utilized a 20 ft. (6.1 m) long×⅛ in. (0.32 cm) diameter tube containing Krytox® perfluorinated polyether on an inert carbon support. The helium flow was 30 mL/min ($5.0(10)^{-7}m^3$/sec). Gas chromatographic conditions were 60° C. for an initial hold period of three minutes followed by temperature programming to 200° C. at a rate of 6° C./minute.

| LEGEND | |
|---|---|
| 215aa is $CF_3CCl_2CClF_2$ | 216aa is $CF_3CCl_2CF_3$ |
| 215bb is $CF_3CFClCFCl_2$ | 225da is $CF_3CHClCClF_2$ |
| 226da is $CF_3CHClCF_3$ | 1213xa is $CF_3CCl=CCl_2$ |
| 1214 is $C_3Cl_2F_4$ | 1215xc is $CF_3CCl=CF_2$ |

TABLE 1

| Ex. No. | Prep. No. | T °C. | 1215xc | 226da | 216aa | 1214 | 225da | 215aa | 215bb | 1213xa |
|---|---|---|---|---|---|---|---|---|---|---|
| 1 | 1 | 280 | 17.9 | 64.8 | 5.0 | 4.0 | 3.5 | 1.2 | ND | 2.8 |
|   |   | 320 | 8.3 | 85.0 | 3.1 | 1.8 | 0.6 | 0.2 | ND | 0.8 |
| 2 | 2 | 280 | 3.1 | 90.9 | 3.2 | 0.5 | 0.9 | 0.6 | ND | 0.4 |
|   |   | 300 | 1.3 | 93.5 | 3.8 | 0.2 | 0.2 | 0.4 | ND | 0.2 |
|   |   | 320 | 1.7 | 93.7 | 3.3 | 0.3 | 0.2 | 0.2 | ND | 0.2 |
| 3 | 3 | 280 | 25.0 | 57.1 | 4.5 | 4.9 | 5.2 | 1.1 | ND | 2.1 |
|   |   | 320 | 8.5 | 83.3 | 4.4 | 2.1 | 0.6 | 0.3 | ND | 0.8 |
| 4 | 4 | 280 | 53.3 | 7.3 | 2.7 | 11.5 | 3.6 | 2.5 | 1.2 | 17.7 |
|   |   | 320 | 62.2 | 12.3 | 2.5 | 13.3 | 2.7 | 0.9 | ND | 6.0 |
| 5 | 5 | 280 | 53.7 | 12.8 | 2.4 | 12.0 | 5.5 | 1.9 | ND | 11.1 |
|   |   | 320 | 59.4 | 14.2 | 1.7 | 13.9 | 3.8 | 0.1 | ND | 6.3 |
|   |   | 350 | 56.7 | 21.7 | 3.5 | 11.0 | 1.8 | ND | ND | 3.4 |
| 6 | 6 | 280 | 51.8 | 23.6 | 3.9 | 7.8 | 3.9 | 1.5 | ND | 7.2 |
|   |   | 320 | 49.0 | 29.0 | 4.0 | 10.3 | 2.4 | 0.4 | ND | 4.8 |
| Comp. Ex. |   | 300 | ND | 89.7 | 7.8 | ND | ND | ND | ND | ND |

ND = not detected

Examination of the data in the fluorination examples above show that the fluorine content of the starting CFC-1213xa is increased to produce CFC-1215xc, HCFC-226da as well as other useful products containing a higher fluorine content than the starting material by using the catalysts of this invention. The $CF_3CCl{=}CF_2$ and $CF_3CHClCF_3$ produced above may be hydrogenated to $CF_3CH_2CHF_2$ and $CF_3CH_2CF_3$, respectively, in accordance with the teachings of U. S. Pat. No. 5,523,501 for the hydrogenolysis of halofluorocarbons containing 3 or 4 carbon atoms using palladium supported on carbon. The $CF_3CH_2CHF_2$ and $CF_3CH_2CF_3$ may then be delivered in the vapor phase to a dehydrofluorination catalyst to produce $CF_3CH{=}CHF$ and $CF_3CH{=}CF_2$, respectively, according to the teachings described in U. S. Pat. No. 6,369,284. The $CF_3CH{=}CHF$ and $CF_3CH{=}CF_2$ may be sent to a separation unit to recover $CF_3CH{=}CHF$ and $CF_3CH{=}CF_2$ individually or as mixtures of $CF_3CH{=}CHF$ and $CF_3CH{=}CF_2$ using procedures well known to the art.

What is claimed is:

1. A process for the manufacture of at least one compound selected from the group consisting of 1,3,3,3-tetrafluoropropene and 1,1,3,3,3-pentafluoropropene, comprising:

(a) reacting HF and at least one halopropene of the formula $CX_3CCl{=}CClX$, wherein each X is independently selected from the group consisting of F and Cl, to produce a product comprising $CF_3CCl{=}CF_2$ and $CF_3CHClCF_3$, wherein said $CF_3CCl{=}CF_2$ and $CF_3CHClCF_3$ are produced in the presence of a fluorination catalyst comprising at least one chromium-containing component selected from (i) a crystalline alpha-chromium oxide where at least 0.05 atom % of the chromium atoms in the alpha-chromium oxide lattice are replaced by divalent copper, and (ii) a chromium-containing composition of (i) which has been treated with a fluorinating agent;

(b) reacting $CF_3CCl{=}CF_2$, $CF_3CHClCF_3$ or both $CF_3CCl{=}CF_2$ and $CF_3CHClCF_3$ produced in (a) with hydrogen, optionally in the presence of HF, to produce a product comprising at least one compound selected from the group consisting of $CF_3CH_2CHF_2$ and $CF_3CH_2CF_3$;

(c) dehydrofluorinating at least one compound selected from the group consisting of $CF_3CH_2CHF_2$ and $CF_3CH_2CF_3$ produced in (b), to produce a product comprising at least one compound selected from the group consisting of $CF_3CH{=}CHF$ and $CF_3CH{=}CF_2$; and (d) recovering at least one compound selected from the group consisting of $CF_3CH{=}CHF$ and $CF_3CH{=}CF_2$ from the product produced in (c).

2. The process of claim 1 wherein the amount of copper relative to the total of chromium and copper in the alpha-chromium oxide is from about 1 atom % to about 5 atom %.

3. The process of claim 1 wherein in (b) both $CF_3CCl{=}CF_2$ and $CF_3CHClCF_3$ produced in (a) are reacted with hydrogen to produce a product comprising both $CF_3CH_2CHF_2$ and $CF_3CH_2CF_3$; wherein in (c) both $CF_3CH_2CHF_2$ and $CF_3CH_2CF_3$ produced in (b) are dehydrofluorinated to produce a product comprising both $CF_3CH{=}CHF$ and $CF_3CH{=}CF_2$; wherein in (d) $CF_3CH{=}CF_2$ is recovered; and wherein $CF_3CH{=}CHF$ is further processed to produce $CF_3CH_2CH_2F$ by hydrogenation.

4. The process of claim 1 wherein in (b) both $CF_3CCl{=}CF_2$ and $CF_3CHClCF_3$ produced in (a) are reacted with hydrogen to produce a product comprising both $CF_3CH_2CHF_2$ and $CF_3CH_2CF_3$; wherein in (c) both $CF_3CH_2CHF_2$ and $CF_3CH_2CF_3$ produced in (b) are dehydrofluorinated to produce a product comprising both $CF_3CH{=}CHF$ and $CF_3CH{=}CF_2$; wherein in (d) $CF_3CH{=}CHF$ is recovered; and wherein $CF_3CH{=}CF_2$ is returned to the step (b) reaction zone to produce additional $CF_3CH_2CHF_2$ by hydrogenation.

* * * * *